United States Patent
Marshall et al.

(10) Patent No.: US 9,086,349 B1
(45) Date of Patent: Jul. 21, 2015

(54) SAMPLE DIGESTER WITH INDEPENDENTLY CONTROLLABLE SAMPLE TEMPERATURE AND ULTRAVIOLET IRRADIATION

(71) Applicants: Graham D. Marshall, Fox Island, WA (US); Duane K. Wolcott, Fox Island, WA (US); David J. Holdych, Gig Harbor, WA (US)

(72) Inventors: Graham D. Marshall, Fox Island, WA (US); Duane K. Wolcott, Fox Island, WA (US); David J. Holdych, Gig Harbor, WA (US)

(73) Assignee: GlobalFIA, INC., Fox Island, WA (US)

( * ) Notice: Subject to any disclaimer, the term of this patent is extended or adjusted under 35 U.S.C. 154(b) by 62 days.

(21) Appl. No.: 13/904,571

(22) Filed: May 29, 2013

(51) Int. Cl.
*B01L 3/14* (2006.01)
*G01N 1/44* (2006.01)

(52) U.S. Cl.
CPC ........................................ *G01N 1/44* (2013.01)

(58) Field of Classification Search
CPC ..... B01J 19/123; B01L 3/5027; G01N 21/05; G01N 21/33
USPC ............................................. 422/22, 24, 549
See application file for complete search history.

(56) References Cited

U.S. PATENT DOCUMENTS

| | | | |
|---|---|---|---|
| 4,000,407 A * | 12/1976 | Keller et al. | 362/218 |
| 5,372,781 A | 12/1994 | Hallett et al. | |
| 5,398,559 A * | 3/1995 | Westlake et al. | 73/863.81 |
| 5,416,576 A * | 5/1995 | Westlake et al. | 356/246 |
| 5,505,912 A | 4/1996 | Hallett | |
| 6,054,097 A | 4/2000 | Mass et al. | |
| 6,972,415 B2 | 12/2005 | Schaible et al. | |
| 7,391,041 B2 | 6/2008 | Sajo et al. | |
| 7,691,342 B2 | 4/2010 | Sahle-Messie et al. | |
| 7,993,580 B2 | 8/2011 | Anderle et al. | |
| 8,377,375 B2 | 2/2013 | Anderle et al. | |

* cited by examiner

*Primary Examiner* — Dennis M White
*Assistant Examiner* — Bryan Kilpatrick
(74) *Attorney, Agent, or Firm* — Reginald F. Roberts, Jr.

(57) ABSTRACT

A sample digester with independently controllable sample heating and ultraviolet radiation. There are two unique advantages. Because the two digestion means are independent, the user can optimize the means of digestion to suit the analytical method. A second advantage is that the ultraviolet source can be maintained at a relatively cool temperature, for which the greatest amount of light is transmitted. Since both means of digestion can be carried out simultaneously, there is a substantial saving of time and a significant improvement in digestion efficiency.

2 Claims, 1 Drawing Sheet

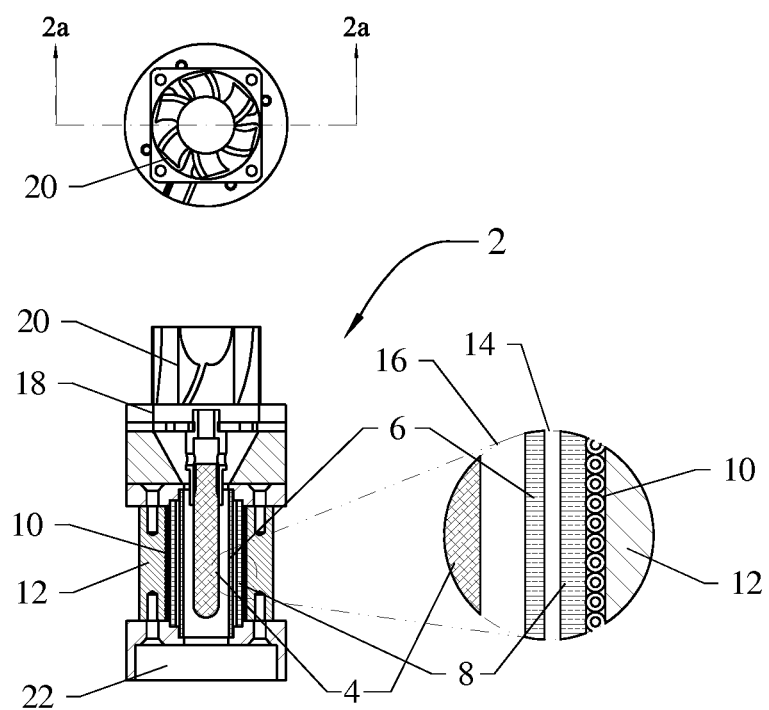

SAMPLE DIGESTER WITH INDEPENDENTLY CONTROLLABLE SAMPLE TEMPERATURE AND ULTRAVIOLET IRRADIATION

BACKGROUND OF THE INVENTION

The present invention relates to sample digestion. More particularly, the invention relates to the combined use of temperature and ultraviolet radiation to digest a sample prior to analysis.

Many chemical and biological assays and treatments require both heating a sample and exposing the sample to ultraviolet light to alter the sample constituents into an acceptable form for the desired application.

Previous digesters that require both heating and ultraviolet exposure have relied upon either of the following methods. In the first method, the sample is held at an elevated temperature for an extended period of time either before or after being moved to an ultraviolet digester for an extended period of time; see, e.g., scientific journal articles by Fernando et al. and by Benson et al., discussed below. This method requires the additional time associated with performing thermal and ultraviolet digestion separately and sequentially.

In the second method, the sample is placed in intimate contact with the ultraviolet source, and the sample comes to the same temperature as the source; see, e.g., U.S. Pat. Nos. 7,391,041, 7,993,580, and 8,377,375, and Publication JP 2011181266, discussed below. The disadvantage of this method is that the source and the sample must be at or near the same temperature. Often the temperature of a sample must be raised significantly in order to obtain the desired effects of thermal digestion. If the mercury ultraviolet source is allowed to reach these higher temperatures, the efficiency of the source will decrease due to self-absorption of mercury emission by volatilized mercury, thereby resulting in smaller contributions from the ultraviolet (UV) digestion.

U.S. Pat. No. 7,391,041 discloses means for heating a UV lamp to enhance emitting efficiency of the lamp. It is apparent that the means chosen, in which the heating means are applied directly to the envelope or envelopes surrounding the UV lamp would, in the case of the outer envelope, heat the sample fluid in contact with the outer envelope. Furthermore, heating the sample fluid would necessarily heat the UV lamp, and heating the UV lamp would necessarily heat the sample fluid.

U.S. Pat. Nos. 7,993,580 and 8,377,375 disclose the use of thermostatted lamps. However, this arrangement relates only to the temperature of the lamp, not to the temperature of the sample.

Publication JP 2011181266 teaches controlling lamp temperature by use of heat-resistant plates and by varying the volume of wind through the apparatus. As in the case of the two patents just discussed above, the only feature of the apparatus that is affected is the temperature of the lamp.

Fernandes, Lima, and Rangel [*J. Anal. Chem* (2000) 366: 112-115] describe a method using a two-stage photooxidation/thermal-digestion procedure in which polyphosphates are hydrolyzed with acid and heat, and organophosphates are digested by UV-catalyzed peroxydisulfate oxidation. Clearly, this stagewise procedure requires sequential time expenditures.

Benson, McKelvie, Hart, Truong, and Hamilton [*Analytica Chimica Acta* 326 (1996) 29-39] describe a method using UV/thermal-induced digestion by means of a UV photoreactor and a thermal-digestion unit connected in series. Clearly, this method likewise suffers the disadvantage of sequential time expenditures.

SUMMARY OF THE INVENTION

In general, the present invention provides a sample digester with independently controllable sample temperature and irradiation. In a first aspect, the sample digester comprises
  (a) a lamp for irradiating the sample;
  (b) first and second members, concentric with the lamp and with one another, the members defining therebetween a space, the first member being nearer the lamp than the second member, the members being transparent to a chosen radiation, providing an air channel therebetween for cooling the lamp, and preventing or minimizing heat transfer across the space separating the members;
  (c) a segment of tubing transparent to the chosen irradiation, the tubing being coiled around the second member, for holding a sample; and
  (d) a heater concentric with the lamp and with the first and second members, for heating the sample to a chosen temperature independently of the lamp and without raising temperature of the lamp.

In a second aspect, the sample digester comprises
  (a) independent means for irradiating a sample independently of sample temperature; and
  (b) independent means for heating the sample independently of irradiation of the sample.

BRIEF DESCRIPTION OF THE DRAWINGS

FIG. 1 is a cross-sectional schematic representation of a sample digester, made in accordance with the principles of the present invention, taken along the cutting line 2a-2a.

DETAILED DESCRIPTION OF THE DISCLOSED EMBODIMENTS

The present invention enables simultaneous and independent heating and irradiation of a chemical or biological sample while maintaining maximum lamp intensity.

Reference is now made to FIG. 1, in which is shown a cross-sectional view of a sample digester, made in accordance with the principles of the present invention, and generally designated by the numeral 2. The sample digester 2 comprises a cylindrical ultraviolet lamp 4 for irradiating a sample. An annular air channel 16 surrounds the lamp 4. First and second pieces of quartz 6 and 8, separated by an air gap 14, surround the air channel 16, allowing ultraviolet light to pass outward through the quartz while limiting heat transmission across the quartz pieces. A length of ultraviolet-transparent tubing 10, for holding the sample, is wrapped about the outer quartz piece 8. A cylindrical heater 12 is wrapped around the outside of the tubing 10 to heat the sample. At one end 18 of the sample digester 2 is a fan 20 to draw air from the other end 22, which is open to the environment, through the air channel 16, to provide a flow of air between the first and second pieces of quartz 6, 8, and over the lamp 4, to limit heat transfer between the heater 12 and the sample, and to cool the lamp 4. Air can be either drawn or blown through the air channel 16; the direction of the air flow is not significant.

The previously unknown feature of the present invention is decoupling the applied thermal energy used for thermal digestion and the ultraviolet output of the ultraviolet source, thus allowing and enabling simultaneous and independent thermal and photochemical digestion.

The invention has two unique advantages. The first advantage is that the thermal and ultraviolet exposure of the sample can be controlled independently of one another. Because the two means of sample decomposition are separate and independent, the user can optimize the means of digestion to suit the analytical method. The second advantage is that the ultraviolet source can be maintained at the optimum temperature for which the maximum light is transmitted to the sample while the sample is held at a relatively high temperature to facilitate and accelerate thermal digestion. Thus, the combination of higher ultraviolet light intensity and higher temperature results in a faster rate of digestion.

While certain specific details and embodiments have been described to illustrate the principles of the present invention, it will be apparent to those skilled in the art that many modifications are possible within the scope of the disclosed invention.

What is claimed is:

1. A sample digester with independently controllable sample temperature and irradiation, the sample digester comprising:
   (a) an ultraviolet lamp for irradiating the sample;
   (b) first and second members, concentric with the lamp and with one another, the members defining therebetween a space, the first member being nearer the lamp than the second member, the members being transparent to a chosen radiation, providing an air channel therebetween for cooling the lamp, and preventing or minimizing heat transfer across the space separating the members;
   (c) a segment of tubing transparent to the chosen irradiation, the tubing being coiled around the second member, for holding a sample; and
   (d) a cylindrical heater concentric with the lamp and with the first and second members, the heater being wrapped around the segment of tubing and the sample, for concurrently heating the sample to a chosen temperature independently of the lamp and without raising temperature of the lamp.

2. A sample digester with independently controllable sample temperature and irradiation, the sample digester comprising:
   (a) independent means for irradiating a sample with ultraviolet radiation independently of sample temperature; and
   (b) independent means for concurrently heating the sample independently of irradiation of the sample;
   wherein the independent heating and irradiation means include an ultraviolet lamp for irradiating the sample; first and second members, concentric with the lamp and with one another, the members defining therebetween a space, the first member being nearer the lamp than the second member, the members being transparent to a chosen radiation, providing an air channel therebetween for cooling the lamp, and preventing or minimizing heat transfer across the space separating the members; a segment of tubing transparent to the chosen irradiation, the tubing being coiled around the second member, for holding a sample; and a cylindrical heater concentric with the lamp and with the first and second members, the heater being wrapped around the segment of tubing and the sample, for concurrently heating the sample to a chosen temperature independently of the lamp and without increasing temperature of the lamp.

* * * * *